(12) United States Patent
Yu et al.

(10) Patent No.: US 9,951,370 B2
(45) Date of Patent: Apr. 24, 2018

(54) CHEMICAL INDICATING COMPOSITION, AUTOCLAVE PROCESS INDICATOR AND METHOD FOR PREPARING AUTOCLAVE PROCESS INDICATOR

(71) Applicant: 3M INNOVATIVE PROPERTIES COMPANY, St. Paul, MN (US)

(72) Inventors: Liwei Yu, Shanghai (CN); Kai Qiu, Shanghai (CN)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/508,295

(22) PCT Filed: Oct. 8, 2015

(86) PCT No.: PCT/US2015/054603
§ 371 (c)(1),
(2) Date: Mar. 2, 2017

(87) PCT Pub. No.: WO2016/057741
PCT Pub. Date: Apr. 14, 2016

(65) Prior Publication Data
US 2017/0283848 A1 Oct. 5, 2017

(30) Foreign Application Priority Data
Oct. 9, 2014 (CN) .......................... 2014 1 0528329

(51) Int. Cl.
| | | |
|---|---|---|
| *G01N 31/22* | (2006.01) | |
| *G01N 21/78* | (2006.01) | |
| *A61L 2/07* | (2006.01) | |
| *A61L 2/28* | (2006.01) | |
| *C09D 11/50* | (2014.01) | |
| *C12Q 1/22* | (2006.01) | |
| *G01N 21/81* | (2006.01) | |

(52) U.S. Cl.
CPC .................. *C12Q 1/22* (2013.01); *A61L 2/07* (2013.01); *A61L 2/28* (2013.01); *G01N 21/78* (2013.01); *G01N 31/226* (2013.01); *G01N 21/81* (2013.01)

(58) Field of Classification Search
CPC .... A61L 2/28; A61L 2/07; C12Q 1/22; G01N 31/226; G01N 21/81; G01N 21/78; C09D 11/50
See application file for complete search history.

(56) References Cited

U.S. PATENT DOCUMENTS

| | | |
|---|---|---|
| 2,889,799 A | 6/1959 | Korpman |
| 3,360,338 A | 12/1967 | Edenbaum |
| 3,471,422 A | 10/1969 | Edlein |
| 4,179,397 A | 12/1979 | Rohowetz |
| 5,057,433 A | 10/1991 | Douglas |
| 5,064,576 A | 11/1991 | Suto |
| 5,087,659 A | 2/1992 | Fujisawa |
| 5,916,816 A | 6/1999 | Read |
| 5,990,199 A | 11/1999 | Bealing |
| 2003/0113923 A1 | 6/2003 | Puntambekar |
| 2004/0241862 A1 | 12/2004 | Puntambekar |
| 2014/0370604 A1* | 12/2014 | Landgrebe ............. C09D 11/50 436/1 |
| 2015/0004706 A1* | 1/2015 | Nair .......................... A61L 2/28 436/1 |

FOREIGN PATENT DOCUMENTS

| | | |
|---|---|---|
| CA | 1336225 | 7/1995 |
| CN | 102947698 | 2/2013 |
| EP | 2153853 | 2/2010 |
| GB | 872136 | 7/1961 |
| JP | S55-40861 | 3/1980 |
| JP | 61-287972 | 12/1986 |
| JP | 2-180973 | 7/1990 |
| JP | 2-21162 | 8/1990 |
| JP | 2001-122348 | 5/2001 |
| JP | 2002-80756 | 3/2002 |
| JP | 2006-104346 | 4/2006 |
| JP | 2007-333620 | 12/2007 |
| JP | 2008-32599 | 2/2008 |
| JP | 2008-132311 | 6/2008 |
| JP | 2009-31273 | 2/2009 |
| JP | 2010-71883 | 4/2010 |
| WO | WO 1996-33242 | 10/1996 |
| WO | WO 1998-13431 | 4/1998 |
| WO | WO 2001-086289 | 11/2001 |
| WO | WO 2010-078422 | 7/2010 |
| WO | WO 2013-096299 | 6/2013 |
| WO | WO 2014-106020 | 7/2014 |

OTHER PUBLICATIONS

International Search report for PCT International Application No. PCT/US2015/054603 dated Nov. 23, 2015, 4 pages.

* cited by examiner

*Primary Examiner* — Jennifer Wecker
(74) *Attorney, Agent, or Firm* — 3M Innovative Properties Company; Carlos M. Téllez

(57) ABSTRACT

A chemical indicating composition. The composition can include an aqueous resin in a form of polymer emulsion or polymer dispersion, the aqueous resin comprising a first aqueous resin composition and a second aqueous resin composition; a film-forming agent; a color changing composition; and water as a solvent. The chemical indicating composition of this disclosure can be used in an autoclave process indicator.

20 Claims, No Drawings

CHEMICAL INDICATING COMPOSITION, AUTOCLAVE PROCESS INDICATOR AND METHOD FOR PREPARING AUTOCLAVE PROCESS INDICATOR

CROSS REFERENCE TO RELATED APPLICATIONS

This application is a national stage filing under 35 U.S.C. 371 of PCT/US2015/054603, filed Oct. 8, 2015, which claims the benefit of Chinese Application No. 201410528329.5, filed Oct. 9, 2014, the disclosure of which is incorporated by reference in its entirety herein.

FIELD OF THE ART

The present disclosure relates to an autoclave process indicator, and more specifically, to a chemical indicating composition for an autoclave process indicator, an autoclave process indicator utilizing the chemical indicating composition, and a method for preparing the autoclave process indicator.

BACKGROUND

The autoclaving process is generally defined as a high-temperature damp-heat (steam) process for completely destroying all viable microorganisms including organisms such as viruses and spores. Considering the possible infection risk associated with improper sterilization (i.e. failing to reach the sterilization condition), monitoring the sterilization process is always beneficial. Standard practice involves sterilizing the articles to be sterilized in the presence of an indicator, and then evaluating the sterilization process based on the change occurred to the indicator (affected by one or more sterilization condition(s)). Currently there are two general types of autoclave indicators, i.e. biological indicators and chemical indicators. Because a relatively longer period is needed to read the result of biological indicators after sterilization, chemical indicators, which can be read at the end of the sterilization process right away, have become very popular for the normal operation in hospitals, clinics and the like.

In some existing chemical indicating systems, an indicating composition using a nitrocellulose resin system as described in U.S. Pat. No. 288,979 and GB872136 is employed. Such an indicating composition is based on an organic thermochromic dye, or a derivative thereof, or a metallic salt compound, and can be coated on a paper substrate so as to make an autoclave tape.

Most of the existing indicators are based on the use of organic solvents such as ketones, hydrocarbons, alcohols, or esters, which can harm the environment and cause safety issues associated with manufacturing and handling.

SUMMARY

The present disclosure provides an aqueous resin based chemical indicating composition that causes an optical density change during exposure to autoclaving conditions and that possesses good steam resistance and low transfer of indicating composition to other surfaces.

Some aspects of the present disclosure provide a chemical indicating composition comprising: an aqueous resin in a form of polymer emulsion or polymer dispersion, having a molecular weight of 20,000 or more and an acid value of 60 or less, the aqueous resin comprising a first aqueous resin composition having a minimum film-forming temperature of 30° C. or more and a second aqueous resin composition having a minimum film-forming temperature lower than 30° C.; a film-forming agent; a color changing composition; and water as a solvent, wherein, based on total weight of the chemical indicating composition, the solid weight percentage of the first aqueous resin composition is 10-30%, the solid weight percentage of the second aqueous resin composition is 0-35%, the weight percentage of the film-forming agent is 1-10%, the weight percentage of the color changing composition is 15-40%, the total weight percentage of the water contained in the aqueous resin composition and the water as a solvent is 20-70%, and the solid content of the aqueous resin composition and the color changing composition are in a weight ratio of 1:3 or more.

Some aspects of the present disclosure provide an autoclave process indicator comprising a substrate and a chemical indicating composition of the present disclosure coated on the substrate.

Some aspects of the present disclosure provide a method for preparing an autoclave process indicator. The method can include coating a chemical indicating composition of the present disclosure onto a surface of a substrate to form an autoclave process indicator.

Chemical indicating compositions of the present disclosure can be used as an autoclave process indicator. In addition, the chemical indicating compositions of the present disclosure have good adhesion to the substrate, such that the chemical indicating composition can be coated on the substrate to prepare an autoclave process indicator. In some embodiments, the chemical indicating composition can also have good water resistance. In some embodiments, the chemical indicating composition can cause less contamination to an adhesive employed in the autoclave process indicator, due to the low transfer of the chemical indicating composition to the adhesive. In some embodiments, the transfer of the chemical indicating composition to a sterilization wrap is also low, and thus less contamination is caused to the wrap. Furthermore, in some embodiments, chemical indicating compositions of the present disclosure are aqueous systems with low viscosity and high solid content, and consequently, are environmentally friendly and safe to handle.

DETAILED DESCRIPTION

It should be understood that, according to the teachings of the present description, a person skilled in the art may contemplate other embodiments and be capable of modifying them, without departing from the scope or spirit of the present disclosure. Therefore, the following specific embodiments are not to be taken in a limiting sense.

Unless otherwise indicated, all numbers expressing feature sizes, amounts and physical properties used in the present specification and claims are to be understood as being modified in all instances by the term "about". Accordingly, unless indicated to the contrary, all numerical parameters set forth in the foregoing specification and claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.1, 1.3, 1.5, 2, 2.75, 3, 3.80, 4, 5, and so on) and any range within that range.

Chemical Indicating Composition

In some embodiments, the chemical indicating composition provided in present disclosure comprises:

an aqueous resin in a form of polymer emulsion or polymer dispersion, having a molecular weight of 20,000 or more and an acid value of 60 or less, the aqueous resin composition comprising a first aqueous resin composition having a minimum film-forming temperature of 30° C. or more and a second aqueous resin composition having a minimum film-forming temperature lower than 30° C.;

a film-forming agent;

a color changing composition; and water as a solvent, wherein, based on total weight of the chemical indicating composition, the solid weight percentage of the first aqueous resin composition is 10-30%, the solid weight percentage of the second aqueous resin composition is 0-35%, the weight percentage of the film-forming agent is 1-10%, the weight percentage of the color changing composition is 15-40%, the total weight percentage of the water contained in the aqueous resin and the water as a solvent is 20-70%, and the solid content of the aqueous resin and the color changing composition are in a weight ratio of 1:3 or more.

Aqueous Resin

An aqueous resin in a form of polymer emulsion or polymer dispersion is used in the present disclosure. In this disclosure, "polymer emulsion" and "polymer dispersion" can be used interchangeably.

The aqueous resin has a molecular weight of 20,000 or more; in some embodiments, the aqueous resin has a molecular weight of 100,000 or more; and in some embodiments, the aqueous resin has a molecular weight of 200,000 or more, so that the chemical indicating composition has good adhesion to the substrate, The aqueous resin has an acid value of 60 or less, in some embodiments the aqueous resin has an acid value of 50 or less, so that the chemical indicating composition has good water resistance.

The aqueous resin comprises a first aqueous resin composition. The first aqueous resin composition may be at least one selected from the group consisting of acrylic polymer emulsion or polymer dispersion, polyurethane polymer emulsion or polymer dispersion, and a combination thereof. The acrylic polymer emulsion or polymer dispersion may be at least one selected from the group consisting of anionic acrylic polymer emulsion or polymer dispersion, styrene acrylic polymer emulsion or polymer dispersion, silicone modified acrylic polymer emulsion or polymer dispersion, acrylic modified polyurethane polymer emulsion or polymer dispersion, silicone modified polyurethane polymer emulsion or polymer dispersion, polycarbonate modified polyurethane polymer emulsion or polymer dispersion, and a combination thereof. The polyurethane resin polymer emulsion or polymer dispersion may be at least one selected from the group consisting of acrylic modified polyurethane polymer emulsion or polymer dispersion, silicone modified polyurethane polymer emulsion or polymer dispersion, polycarbonate modified polyurethane polymer emulsion or polymer dispersion, and a combination thereof. The first aqueous resin composition has a minimum film-forming temperature (MFT) of 30° C. or more, in some embodiments 60° C. or more. The non-limiting examples of the first aqueous resin composition include NeoCryl A-1131 (anionic acrylic polymer emulsion), NeoCryl XK-52 (anionic methacrylic polymer emulsion), and NeoCryl A-1091 (anionic styrene acrylic polymer emulsion) manufactured by DSM; and Joncryl HPE 2157 (styrene acrylic polymer emulsion) and SILIKOPUR 8080 (silicone modified polyurethane polymer emulsion) manufactured by BASF. In some embodiments, the first aqueous resin composition has a molecular weight of 20,000 or more; in some embodiments, the first aqueous resin composition has a molecular weight of 100,000 or more; and in some embodiments, the first aqueous resin composition has a molecular weight of 200,000 or more. In some embodiments, the first aqueous resin composition has an acid value of 60 or less; in some embodiments, the first aqueous resin composition has an acid value of 50 or less.

The solid content of the first aqueous resin composition is 10-30% by weight, based on total weight of the chemical indicating composition. If the solid content (solid weight percentage) of the first aqueous resin composition is too low, such as less than 10%, the chemical indicating composition on the side of the non-adhesive surface of an autoclaving indicator tape may, in the case where the autoclaving indicator tape containing the chemical indicating composition is wound up, transfer to the adhesive surface of the autoclaving indicator tape wound thereon, thereby causing the contamination of the chemical indicating composition to the adhesive surface. If the solid content of the first aqueous resin composition is too high, such as greater than 30%, the aqueous resin composition may not present in a form of polymer emulsion or polymer dispersion.

Optionally, the aqueous resin may further comprise a second aqueous resin composition. The second aqueous resin composition may be at least one selected from the group consisting of acrylic polymer emulsion or polymer dispersion, polyurethane polymer emulsion or polymer dispersion, and a combination thereof. The acrylic polymer emulsion or polymer dispersion may be at least one selected from the group consisting of anionic acrylic polymer emulsion or polymer dispersion, styrene acrylic polymer emulsion or polymer dispersion, silicone modified acrylic polymer emulsion or polymer dispersion, acrylic modified polyurethane polymer emulsion or polymer dispersion, silicone modified polyurethane polymer emulsion or polymer dispersion, polycarbonate modified polyurethane polymer emulsion or polymer dispersion, and a combination thereof. The polyurethane resin polymer emulsion or polymer dispersion may be at least one selected from the group consisting of acrylic modified polyurethane polymer emulsion or polymer dispersion, silicone modified polyurethane polymer emulsion or polymer dispersion, polycarbonate modified polyurethane polymer emulsion or polymer dispersion, and a combination thereof. The second aqueous resin composition has a minimum film-forming temperature lower than 30° C. The non-limiting examples of the second aqueous resin composition include NeoCryl A-2092 (acrylic styrene polymer emulsion), NeoCryl A-2099 (acrylic styrene polymer emulsion), NeoCryl A-1127 (self-crosslinking acrylic polymer emulsion), NeoPac E-200 (acrylic modified polyurethane polymer emulsion), NeoRez R-650 (polyurethane polymer dispersion), NeoRez R-986 (anionic aliphatic polycarbonate polymer emulsion) manufactured by DSM, and Joncryl 77 (styrene acrylic polymer emulsion), Acronal TL8821 (styrene acrylic polymer emulsion) manufactured by BASF. In some embodiments, the second aqueous resin composition has a molecular weight of 20,000 or more; in some embodiments, the second aqueous resin composition has a molecular weight of 100,000 or more; and in some embodiments, the second aqueous resin composition has a molecular weight of 200,000 or more. In some embodiments, the second aqueous resin composition has an acid value of 60 or less; in some embodiments, the second aqueous resin composition has an acid value of 50 or less.

The solid content of the second aqueous resin composition is 0-35% by weight, based on total weight of the chemical indicating composition. The second aqueous resin composition has a relative lower minimum film-forming temperature and a relative flexible molecular chain, which contributes to the wetting to the substrate, and thereby improving the adhesion between the chemical indicting composition and the substrate. However, the solid content of the second aqueous resin composition should not be too high, for example, when the solid content of the second aqueous resin composition is higher than 35%, the chemical indicating composition on the autoclave process indicator may, in the case where the autoclave process indicator containing the chemical indicating composition is placed together with the wrapping materials such as gauze, transfer to the adjacent wrapping materials, causing the contamination of the chemical indicating composition to the wrapping materials.

Film-Forming Agent

The chemical indicating composition provided in the present disclosure comprises at least one film-forming agent (also sometimes referred to as a plasticizer). The film-forming agent can accelerate the uniform film-forming through the self-induction of the polymer particles in the aqueous resin composition. In addition, the film-forming agent may assists the chemical indicating composition to wet a substrate, thereby improving the adhesion between the chemical indicting composition and the substrate.

The film-forming agent may be at least one selected from the group consisting of a $C_{6-12}$ organic hydrocarbon compound, a $C_{3-16}$ organic compound containing an alcohol functional group, a $C_{3-16}$ organic compound containing an ether functional group, a $C_{3-16}$ organic compound containing an ester functional group, a $C_{3-16}$ organic compound containing a keto functional group, and a combination thereof. The $C_{6-12}$ organic hydrocarbon compound may be at least one selected from the group consisting of an isoparaffin compound, an alicyclic compound, and a combination thereof. In some embodiments, the film-forming agent may be at least one selected from the group consisting of 2,2,4-trimethyl-1,3-pentanediol mono-isobutyrate, adipic acid diester, dimethyl phthalate, cyclohexanone, ethylene glycol butyl ether, propylene glycol butyl ether, dipropylene glycol butyl ether, propylene glycol, N-methylpyrrolidone, ethylene glycol methyl ether, ethylene glycol ethyl ether, and a combination thereof.

Based on total weight of the chemical indicating composition, the weight percent of the film-forming agent is 1-10%, in some embodiments, the weight percent of the film-forming agent is 2-5%. If the weight percent of the film-forming agent is less than 1%, the adhesion of the chemical indicating composition to the substrate may be not enough; if the weight percent of the film-forming agent is higher than 10%, the chemical indicating composition may be not stable enough, accordingly, the autoclave indicating effect of the chemical indicating composition may be reduced.

Color Changing Composition

In some embodiments, the color changing composition herein means a material that changes color (or experiences an optical density alteration) as a result of exposure to the conditions of autoclaving. In some embodiments, the color changing composition is a polyvalent metal compound-based color changing composition, comprising a polyvalent metal compound, a sulfur source, a compound capable of generating alkaline conditions when exposed to steam at a high temperature, and a combination thereof.

The polyvalent metal compound may be an inorganic salt or alkaline inorganic salt compound of at least one selected from the group consisting of lead, copper, cobalt, nickel, bismuth, calcium, and a combination thereof.

The sulfur source is a substance that provides sulfur reacting with the polyvalent metal compound while exposed to the condition under autoclaving. The sulfur source may be at least one selected from the group consisting of elemental sulfur, a sulfur dye, a sulfur pigment, a thiourea compound, and a combination thereof. The thiourea compound may be at least one selected from the group consisting of 2-methoxyphenyl thiourea, 1-allyl-2-thiourea, methylthiourea, ethylthiourea, anilinothiourea, and a combination thereof.

The compound capable of generating alkaline conditions when exposed to steam at a high temperature may be at least one selected from the group consisting of potassium carbonate, sodium carbonate, lithium carbonate, calcium carbonate, magnesium carbonate, potassium bicarbonate, sodium bicarbonate, and a combination thereof.

Based on total weight of the chemical indicating composition, the weight percent of the color changing composition is 15-40%, in some embodiments 20-35%.

As for the system of a polyvalent metal compound—a sulfur source—a compound capable of generating alkaline conditions when exposed to steam at a high temperature, in some embodiments, the amount ratio of the three components is (2-8):(2-20):(2-20), in some embodiments, the amount ratio of the three components is (3-7):(3-18):(3-18).

Without being bound to any theory, it is believed that the color changing composition can be enveloped by the aqueous resin composition, so that possible damage to the color changing composition due to drying and dehydrating during the film formation can be prevented. In order to ensure that the color changing composition can be enveloped sufficiently by the aqueous resin composition, the aqueous resin composition and the color changing composition are in a weight ratio of 1:3 or more. If the aqueous resin composition and the color changing composition are in a weight ratio less than 1:3, the chemical indicating composition on the side of the non-adhesive surface of an autoclaving indicator tape may, in the case where the autoclaving indicator tape containing the chemical indicating composition is wound up, transfer to the adhesive surface of the autoclaving indicator tape wound thereon, thereby causing the contamination of the chemical indicating composition to the adhesive surface.

Water as a Solvent

In some embodiments, this chemical indicating composition of the invention may comprise water as a solvent. Where the aqueous resin composition has enough water, no additional water as a solvent, needs to be added.

The total amount of water including the water contained in the aqueous resin composition and the water used as a solvent is 20-70% by weight, relative to the total weight of the chemical indicating composition.

Other Components

In some embodiments, this chemical indicating composition may further comprise a water-soluble resin, so as to optimize the dispersion of the color changing composition. The water-soluble resin may be at least one selected from the group consisting of water-soluble ethylcellulose, water-soluble rosin modified resin, polyvinyl alcohol, water-soluble epoxy resin, water-soluble alkyd resin, water-soluble polyester resin, water-soluble polyurethane, water-soluble acrylate resin, and a combination thereof.

Based on total weight of the chemical indicating composition, the weight percent of the water-soluble resin is 0-5%.

In some embodiment, this chemical indicating composition may further comprise an optional auxiliary component. The auxiliary component may be at least one selected from the group consisting of a pH stabilizer, a bactericide, a defoamer, a dispersant, an anti-sticking agent, a leveling agent, a wetting agent, a rheology modifier, a UV light stabilizer, a wax, and a combination thereof. The types and contents of these auxiliaries can be chosen according to actual demands.

Method for Preparing Chemical Indicating Composition

The chemical indicating composition of the present invention is obtained by mixing the components for preparing the chemical indicating composition. For the components of the chemical indicating composition, please see the part of "Chemical indicating composition" in this description.

In some embodiments, the chemical indicating composition may be obtained by placing the components for preparing the chemical indicating composition into a glass jar and grinding using zirconium beads for 48 hours.

Autoclave Process Indicator

The autoclave process indicator provided in the present disclosure comprises a substrate and the chemical indicating composition of the present disclosure coated on the substrate.

For the components of the chemical indicating composition, please see the part of "Chemical indicating composition" in this description.

The substrate may be at least one selected from the group consisting of an adhesive tape, a plastic film, a paper, a nonwoven fabric, and a combination thereof, in some embodiments the substrate comprises an adhesive tape, in some embodiments the substrate comprises a pressure sensitive adhesive tape.

Where the substrate is an adhesive tape, the adhesive tape comprises an adhesive surface and a non-adhesive surface, the chemical indicating composition is coated onto the non-adhesive surface of the adhesive tape, in some embodiment, the chemical indicating composition can be coated onto a release layer of the adhesive tape.

Method for Preparing Autoclave Process Indicator

The method for preparing the autoclave process indicator comprises: coating the chemical indicating composition of the present disclosure onto a surface of a substrate to form an autoclave process indicator.

For the chemical indicating composition, please see the part of "Chemical indicating composition" in this description.

The substrate may be at least one selected from the group consisting of an adhesive tape, a plastic film, a paper, a nonwoven fabric, and a combination thereof, in some embodiments the substrate may be an adhesive tape, in some embodiments the substrate may be a pressure sensitive adhesive tape.

Where the substrate is an adhesive tape, the adhesive tape comprises an adhesive surface and a non-adhesive surface, the chemical indicating composition can be coated onto the non-adhesive surface of the adhesive tape, in some embodiments, the chemical indicating composition can be coated onto a release layer of the adhesive tape.

The method for preparing the autoclave process indicator can further comprise: heating said autoclave process indicator. In some embodiments, the heating temperature is 60° C. or above, in some embodiments, the heating temperature is 100° C. or above.

The following embodiments are intended to be illustrative of the present disclosure and not limiting.

Embodiment 1 relates to a chemical indicating composition, comprising: an aqueous resin in a form of polymer emulsion or polymer dispersion, having a molecular weight of 20,000 or more and an acid value of 60 or less, the aqueous resin comprising a first aqueous resin composition having a minimum film-forming temperature of 30° C. or more and a second aqueous resin composition having a minimum film-forming temperature lower than 30° C., a film-forming agent, a color changing composition, and water as a solvent, wherein, based on total weight of the chemical indicating composition, the solid weight percentage of the first aqueous resin composition is 10-30%, the solid weight percentage of the second aqueous resin composition is 0-35%, the weight percentage of the film-forming agent is 1-10%, the weight percentage of the color changing composition is 15-40%, the total weight percentage of the water contained in the aqueous resin and the water as a solvent is 20-70%, and the solid content of the aqueous resin and the color changing composition are in a weight ratio of 1:3 or greater.

Embodiment 2 relates to the chemical indicating composition according to embodiment 1, wherein the first aqueous resin composition comprises at least one of an acrylic polymer emulsion or polymer dispersion, and a polyurethane polymer emulsion or polymer dispersion.

Embodiment 3 relates to the chemical indicating composition according to embodiment 1 or 2, wherein the first aqueous resin composition comprises at least one of an anionic acrylic polymer emulsion or polymer dispersion, a styrene acrylic polymer emulsion or polymer dispersion, a silicone modified acrylic polymer emulsion or polymer dispersion, an acrylic modified polyurethane polymer emulsion or polymer dispersion, a silicone modified polyurethane polymer emulsion or polymer dispersion, and a polycarbonate modified polyurethane polymer emulsion or polymer dispersion.

Embodiment 4 relates to the chemical indicating composition according to any of the embodiments of 1-3, wherein the second aqueous resin composition comprises at least one of an acrylic polymer emulsion or polymer dispersion, and a polyurethane polymer emulsion or polymer dispersion.

Embodiment 5 relates to the chemical indicating composition according to any of the embodiments of 1-4, wherein the second aqueous resin composition comprises at least one of an anionic acrylic polymer emulsion or polymer dispersion, a styrene acrylic polymer emulsion or polymer dispersion, a silicone modified acrylic polymer emulsion or polymer dispersion, an acrylic modified polyurethane polymer emulsion or polymer dispersion, a silicone modified polyurethane polymer emulsion or polymer dispersion, and a polycarbonate modified polyurethane polymer emulsion or polymer dispersion.

Embodiment 6 relates to the chemical indicating composition according to any of the embodiments of 1-5, wherein the first aqueous resin composition has a molecular weight of 20,000 or more.

Embodiment 7 relates to the chemical indicating composition according to any of the embodiments of 1-5, wherein the first aqueous resin composition has a molecular weight of 100,000 or more.

Embodiment 8 relates to the chemical indicating composition according to any of the embodiments of 1-5, wherein the first aqueous resin composition has a molecular weight of 200,000 or more.

Embodiment 9 relates to the chemical indicating composition according to any of the embodiments of 1-8, wherein the first aqueous resin composition has an acid value of 60 or less.

Embodiment 10 relates to the chemical indicating composition according to any of the embodiments of 1-8, wherein the first aqueous resin composition has an acid value of 50 or less.

Embodiment 11 relates to the chemical indicating composition according to any of the embodiments of 1-10, wherein the second aqueous resin composition has a molecular weight of 20,000 or more.

Embodiment 12 relates to the chemical indicating composition according to any of the embodiments of 1-10, wherein the second aqueous resin composition has a molecular weight of 100,000 or more.

Embodiment 13 relates to the chemical indicating composition according to any of the embodiments of 1-10, wherein the second aqueous resin composition has a molecular weight of 200,000 or more.

Embodiment 14 relates to the chemical indicating composition according to any of the embodiments of 1-13, wherein the second aqueous resin composition has an acid value of 60 or less.

Embodiment 15 relates to the chemical indicating composition according to any of the embodiments of 1-13, wherein the second aqueous resin composition has an acid value of 50 or less.

Embodiment 16 relates to the chemical indicating composition according to any of the embodiments of 1-15, wherein the first aqueous resin composition has a minimum film-forming temperature of 60° C. or more.

Embodiment 17 relates to the chemical indicating composition according to any of the embodiments of 1-16, wherein the film-forming agent comprises at least one of a C6-12 organic hydrocarbon compound, a C3-16 organic compound which contains an alcohol functional group, a C3-16 organic compound which contains an ether functional group, a C3-16 organic compound which contains an ester functional group, and a C3-16 organic compound which contains a keto functional group.

Embodiment 18 relates to the chemical indicating composition according to embodiment 17, wherein the organic hydrocarbon compound comprises at least one of an isoparaffin compound and an alicyclic compound.

Embodiment 19 relates to the chemical indicating composition according to any of the embodiments of 1-17, wherein the film-forming agent comprises at least one of 2,2,4-trimethyl-1,3-pentanediol mono-isobutyrate, adipic acid diester, dimethyl phthalate, cyclohexanone, ethylene glycol butyl ether, propylene glycol butyl ether, dipropylene glycol butyl ether, propylene glycol, N-methylpyrrolidone, ethylene glycol methyl ether, and ethylene glycol ethyl ether.

Embodiment 20 relates to the chemical indicating composition according to any of the embodiments of 1-19, wherein the color changing composition comprises at least one of a polyvalent metal compound, a sulfur source, and a compound capable of generating alkaline conditions when exposed to steam at a high temperature.

Embodiment 21 relates to the chemical indicating composition according to embodiment 20, wherein the polyvalent metal compound, the sulfur source and the compound capable of generating alkaline conditions when exposed to steam at a high temperature are in a ratio of (2-8):(2-20):(2-20).

Embodiment 22 relates to the chemical indicating composition according to embodiment 20, wherein the polyvalent metal compound, the sulfur source and the compound capable of generating alkaline conditions when exposed to steam at a high temperature are in a ratio of (3-7):(3-18):(3-18)

Embodiment 23 relates to the chemical indicating composition according to any of the embodiments of 1-22, wherein the polyvalent metal compound comprises at least one of an inorganic salt of lead, an inorganic salt of copper, an inorganic salt of cobalt, an inorganic salt of nickel, an inorganic salt of bismuth, an inorganic salt of calcium, and an alkaline inorganic salt compound.

Embodiment 24 relates to the chemical indicating composition according to any of the embodiments of 1-23, wherein the sulfur source comprises at least one of elemental sulfur, a sulfur dye, a sulfur pigment, and a thiourea compound.

Embodiment 25 relates to the chemical indicating composition according to embodiment 24, wherein the thiourea compound comprises at least one of 2-methoxyphenyl thiourea, 1-allyl-2-thiourea, methylthiourea, ethylthiourea, and anilinothiourea.

Embodiment 26 relates to the chemical indicating composition according to any of the embodiments of 1-25, wherein the compound capable of generating alkaline conditions when exposed to steam at a high temperature comprises at least one of potassium carbonate, sodium carbonate, lithium carbonate, calcium carbonate, magnesium carbonate, potassium bicarbonate, and sodium bicarbonate.

Embodiment 27 relates to the chemical indicating composition according to any of the embodiments of 1-26, wherein the weight percentage of the film-forming agent is 2-5%.

Embodiment 28 relates to the chemical indicating composition according to any of the embodiments of 1-27, wherein the weight percentage of the color changing composition is 20-35%.

Embodiment 29 relates to the chemical indicating composition according to any of the embodiments of 1-28, further comprising a water-soluble resin in a weight percentage of 0-5%, based on the total weight of the chemical indicating composition.

Embodiment 30 relates to the chemical indicating composition according to embodiment 29, wherein the water-soluble resin comprises at least one of water-soluble ethylcellulose, water-soluble rosin modified resin, polyvinyl alcohol, water-soluble epoxy resin, water-soluble alkyd resin, water-soluble polyester resin, water-soluble polyurethane, and water-soluble acrylate resin.

Embodiment 31 relates to the chemical indicating composition according to any of the embodiments of 1-30, further comprising additive, wherein the additive comprises at least one of pH stabilizer, bactericide, defoamer, dispersant, anti-sticking agent, leveling agent, wetting agent, rheology modifier, UV light stabilizer, and wax.

Embodiment 32 relates to an autoclave process indicator, comprising a substrate and the chemical indicating composition according to any of the embodiment of 1 to 31 coated on the substrate.

Embodiment 33 relates to the autoclave process indicator according to embodiment 32, wherein the substrate comprises at least one of a tape, a plastic film, a paper, and a nonwoven fabric.

Embodiment 34 relates to the autoclave process indicator according to embodiment 32, wherein the substrate comprises an adhesive tape comprising an adhesive surface and a non-adhesive surface, and wherein the chemical indicating composition is coated on the non-adhesive surface of the tape.

Embodiment 35 relates to the autoclave process indicator according to embodiment 32, wherein the substrate comprises an adhesive tape comprising a release layer, and the chemical indicating composition is coated on the release layer of the adhesive tape.

Embodiment 36 relates to a method for preparing the autoclave process indicator according to any of the embodiments of 1-31, the method comprising: coating the chemical indicating composition according to any one of claims 1 to 9 onto a surface of a substrate to form an autoclave process indicator.

Embodiment 37 relates to the method according to embodiment 36, wherein the substrate comprises an adhesive tape comprising an adhesive surface and a non-adhesive surface, and wherein the chemical indicating composition is coated on the non-adhesive surface of the tape.

Embodiment 38 relates to the method according to embodiments 36 or 37, further comprising: heating the autoclave process indicator.

Embodiment 39 relates to the method according to embodiment 38, wherein the heating temperature is 60° C. or above.

The disclosure will be further described in details by incorporating the following Examples. However, the scope of the disclosure is not limited by these specific Examples.

EXAMPLES

Names, functions, chemical names as well as suppliers of the essential component materials used to prepare the chemical indicating composition of the invention, are listed in Table 1.

TABLE 1

| Name | Function | Chemical name | Supplier |
|---|---|---|---|
| Ammonia water | pH stabilizer | Ammonia water | Sinopharm Chemical Reagent, China |
| Propylene glycol | Film-forming agent | Propylene glycol | Sinopharm Chemical Reagent, China |
| Ethylene glycol monomethyl ether | Film-forming agent | Ethylene glycol monomethyl ether | Sinopharm Chemical Reagent, China |
| Propylene glycol butyl ether | Film-forming agent | Propylene glycol butyl ether | Sinopharm Chemical Reagent, China |
| Acronal TL 8821 | Second aqueous resin composition having a MFT of 28° C. | styreneacrylic polyurethane emulsion | BASF, China |
| NeoRez R-986 | Second aqueous resin composition having a MFT lower than 0° C. | anionic aliphatic polycarbonate polymer emulsion | DSM, China |
| NeoCryl A-1131 | First aqueous resin composition having a MFT higher than 81° C. | anionic acrylic polymer emulsion | DSM, China |
| Joncryl 77 | Second aqueous resin composition having a MFT of about 20° C. | styrene acrylic polymer emulsion | BASF, China |
| Joncryl 90 | First aqueous resin composition having a MFT of about 76° C. | styrene acrylic polymer emulsion | BASF, China |
| Joncryl HPE 2157 | First aqueous resin composition having a MFT higher than 85° C. | styrene acrylic polymer emulsion | BASF, China |
| Joncryl 678 | Water-soluble resin | styrene acrylic water-soluble resin | BASF, China |
| BYK 038 | Defoamer | mineral oil defoamer | BYK, China |
| Bismuth Subsalicylate | color changing composition | Bismuth Subsalicylate | Alfa Aesar China |
| Sulfur | color changing composition | sulfur | Pei Xing Company |
| Lithium Carbonate | color changing composition | lithium Carbonate | Pei Xing Company |

The chemical names and physical-chemical features of the aqueous resin compositions used in the Examples are listed in Table 2.

TABLE 2

| Aqueous resin composition | Function | Chemical name | Acid value | Molecular weight (MW) | Minimum Film-forming Temperature (MFT) (° C.) | Glass-transition Temperature (Tg) (° C.) |
|---|---|---|---|---|---|---|
| ACRONAL TL 8821 | Second aqueous resin composition | styreneacrylic copolymer emulsion | — | >100,000 | 28 | — |

TABLE 2-continued

| Aqueous resin composition | Function | Chemical name | Acid value | Molecular weight (MW) | Minimum Film-forming Temperature (MFT) (° C.) | Glass-transition Temperature (Tg) (° C.) |
| --- | --- | --- | --- | --- | --- | --- |
| JONCRYL 77 | Second aqueous resin composition | styreneacrylic copolymer emulsion | 55 | >200,000 | 20 | 21 |
| NeoCryl A-1131 | First aqueous resin composition | anionic acrylic emulsion | 8 | >200,000 | 82 | 65 |
| JONCRYL 90 | First aqueous resin composition | styreneacrylic copolymer emulsion | 76 | >200,000 | >81 | 110 |
| Joncryl HPE 2157 | First aqueous resin composition | styrene acrylic copolymer emulsion | 36 | >200,000 | >85 | 105 |
| NeoRez R-986 | Second aqueous resin composition | anionic polycarbonate dispersion | — | — | <0 | <0 |
| JONCRYL 678 | Water-soluble resin | water-soluble styrene-acrylic resin | 215 | 8,600 | — | 85 |

Preparation of Chemical Indicating Composition

Chemical indicating composition is prepared by placing the components of chemical indicating composition in a glass jar, and grinding using zirconium beads for 48 hours.

Preparation of Autoclave Process Indicator (Autoclave Process Tape/Tag)

The paper tape used in the Examples was Tape 2213 (with a paper substrate) commercially available from 3M. The tag used in the Examples was Polyester Tag 57817 commercially available from 3M.

Preparation of autoclave process tape: the autoclave process tape was obtained by coating, using a green bar #3 (RK Print-Coat Instruments Ltd., UK), chemical indicating composition onto the non-adhesive surface of a paper tape, and drying the coated tape in an oven at 60° C. for 1 min and then at 120° C. for 3 min.

Preparation of autoclave process tag: the autoclave process tag was obtained by coating, using a green bar #3 (RK Print-Coat Instruments Ltd., UK), chemical indicating composition onto a polyester tag surface, and drying the coated label in an oven at 60° C. for 1 min and then at 120° C. for 3 min.

Test for Autoclave Indicating Effect of Chemical Indicating Composition

The testing equipment was a BIER Vessel that meets the ISO 18472 and ISO 11140-1 standards. The coated autoclave process tape was tested while exposed directly to a pre-vacuum sterilization condition. According to ISO 11140-1, the indicating tape is a Class I indicator, and thus was evaluated visually for color change under the conditions of 0.5 min at 134° C. (ISO failure circulation), 2 min at 134° C. (ISO successful circulation), 3 min at 121° C. (ISO failure circulation), 10 min at 121° C. (ISO successful circulation), and 30 min at 140° C. steam-free drying (ISO failure circulation). In accordance with the requirement of ISO 11140-1, the tape changed into a darker color after 2 min at 134° C. than after 0.5 min at 134° C., into a darker color after 10 min at 121° C. than after 3 min at 121° C., and into a lighter color after steam-free drying at 140° C. for 30 min. than under the ISO successful circulation conditions at 134° C. and 121° C. The color intensity was characterized by the color density measured by X-Rite spectrophotometer (X-Rite, Inc. Grand Rapids, Mich., US).

Immediate Adhesion Test (Referred to ASTM D3359 Method)

The masking tape used in the Examples was paper Tape 2213 (with a paper substrate) commercially available from 3M. The tag used in the Examples was Polyester label 57817 (with a polyester substrate) commercially available from 3M.

For coating, a green bar #3 (RK Print-Coat Instruments Ltd., UK) was used. The chemical indicating composition was coated onto the non-pressure sensitive adhesive surface of a masking tape or a polyester tag surface. The coated tape/tag was dried in an oven at 60° C. for 1 min followed by at 120° C. for 3 min.

A blank Tape 2213 was adhered to the coated masking tape or polyester tag with the adhesive surface of the blank Tape 2213 closely contacting with the chemical indicating composition on the masking tape or polyester tag. Subsequently, Tape 2213 was peeled off from the masking tape or polyester tag, and the transfer of the chemical indicating composition from the masking tape or polyester tag to the adhesive of Tape 2213 was evaluated.

For easy observation, the peeled Tape 2213 was subjected to an autoclaving process at 134° C. for 2 min, and then observed whether the chemical indicating composition has been transferred to the adhesive of the blank Tape 2213 (after autoclaving, the transferred chemical indicating composition was blackened).

The test result was scored as follows: 1 (complete transfer of chemical indicating composition), 1.5 (transfer of about 87.5% of chemical indicating composition), 2 (transfer of about 75% of chemical indicating composition), 2.5 (transfer of about 62.5% of chemical indicating composition), 3 (transfer of about 50% of chemical indicating composition), 3.5 (transfer of about 37.5% of chemical indicating composition), 4 (transfer of about 25% of chemical indicating composition), 4.5 (transfer of about 12.5% of chemical indicating composition), and 5 (no transfer of chemical indicating composition).

A higher score indicated a higher adhesion between the chemical indicating composition and the substrate. A chemical indicating composition having a score of 4 or more was regarded as one having good adhesion.

Blocking Test for Transfer of the Chemical Indicating Composition from the Surface of the Autoclave Process Tape to its Adhesive The Tape 2213 used in the example was commercially available from 3M.

A Tape 2213 was adhered to the indicating surface (coated with chemical indicating composition) of the autoclave process tape provided by the present invention, with the adhesive of the Tape 2213 directly contacting with the chemical indicating composition on the autoclave process tape, and then hold under the conditions of 25 Kpa and 54° C. for 48 hrs. Tape 2213 was peeled off from the autoclave process tape. The peeled Tape 2213 was subjected to an autoclaving process at 134° C. for 2 min, and then observed whether the chemical indicating composition has been transferred to the adhesive of the Tape 2213 (after autoclaving, the transferred chemical indicating composition was blackened).

The test result was scored as follows: 1 (complete transfer of chemical indicating composition), 1.5 (transfer of about 87.5% of chemical indicating composition), 2 (transfer of about 75% of chemical indicating composition), 2.5 (transfer of about 62.5% of chemical indicating composition), 3 (transfer of about 50% of chemical indicating composition), 3.5 (transfer of about 37.5% of chemical indicating composition), 4 (transfer of about 25% of chemical indicating composition), 4.5 (transfer of about 12.5% of chemical indicating composition), and 5 (no transfer of chemical indicating composition).

A higher score indicated a lower transfer of the chemical indicating composition to the adhesive. A chemical indicating composition having a score of 4 or more was regarded as one meeting the requirement of low transfer of the chemical indicating composition to the adhesive.

Water Resistance Test of Chemical Indicating Composition

The water resistance test in the present invention comprised wet scuff resistance test and boiling resistance test.

Wet scuff resistance test: the autoclaved indicating surface of the autoclave process indicator (autoclave process tape/tag) was subjected to an autoclaving process at 134° C. for 2 min, and then manually wiped the autoclaved indicating surface using a wet cotton towel for approximately 6 times, and evaluated the abrasion of the chemical indicating composition on the surface of the autoclave process indicator (autoclave process tape/tag).

Boiling resistance test: the autoclaved indicator (autoclave process tape/tag) was kept in a 100° C. water bath for 1 min; then took out and evaluated the transfer of the chemical indicating composition on the surface of the autoclave process indicator (autoclave process tape/tag).

The result of the test was scored as follows: 1 (chemical indicating composition was completely worn out or transferred from substrate), 1.5 (about 87.5% chemical indicating composition was worn out or transferred), 2 (about 75% chemical indicating composition was worn out or transferred), 2.5 (about 62.5% chemical indicating composition was worn out or transferred), 3 (about 50% chemical indicating composition was worn out or transferred), 3.5 (about 37.5% chemical indicating composition was worn out or transferred), 4 (about 25% chemical indicating composition was worn out or transferred), 4.5 (about 12.5% chemical indicating composition was worn out or transferred), and 5 (no abrasion or removal of chemical indicating composition).

A higher score indicated a higher water resistance of the chemical indicating composition. In the wet scuff resistance test, a chemical indicating composition having a score of 4 or more was regarded as one having good wet scuff resistance. In the boiling resistance test, a chemical indicating composition having a score of 3 or more was regarded as one having good boiling resistance.

Transfer Test of the Chemical Indicating Composition to Wrap

The transfer test of the chemical indicating composition to wrap comprises: Step 1), the indicating tape was adhered to a piece of cotton wrap; step 2), the tape was further covered by another piece of cotton wrap (second cotton wrap); step 3), a wrapped towel pack of (Length 9 inch)*(Width 9 inch)*(Height 4 inch) was placed onto the second cotton wrap; and step 4), an autoclaving process was conducted in an autoclave at 134° C. for 10 min, and then the interface between the second cotton wrap and the autoclave process tape was evaluated for transfer level.

The result was scored as follows: 1 (complete transfer of chemical indicating composition), 1.5 (transfer of about 87.5% of chemical indicating composition), 2 (transfer of about 75% chemical indicating composition), 2.5 (transfer of about 62.5% of chemical indicating composition), 3 (transfer of about 50% chemical indicating composition), 3.5 (transfer of about 37.5% of chemical indicating composition), 4 (transfer of about 25% chemical indicating composition), 4.5 (transfer of about 12.5% of chemical indicating composition), and 5 (no transfer of chemical indicating composition).

A higher score indicated a lower transfer of the chemical indicating composition to wrap. A chemical indicating composition having a score of 4 or more was regarded as one meeting the requirement of low transfer of the chemical indicating composition to wrap.

Comparative Examples 1-10 and Examples 1-7

Following the procedure described above, chemical indicating compositions 1-17 were prepared by placing the components, according to the formulations shown in Tables 3, 4, 5-1 and 5-2, in glass jars, and grinding using zirconium beads for 48 hours, wherein, chemical indicating compositions 1-10 were used in Comparative Examples 1-10, and chemical indicating compositions 11-17 were used in Examples 1-7.

TABLE 3

|  | Comparative Example 1 | Comparative Example 2 | Comparative Example 3 | Comparative Example 4 | Comparative Example 5 | Comparative Example 6 |
| --- | --- | --- | --- | --- | --- | --- |
| Bismuth Subsalicylate | 4.5 | 4.5 | 4.5 | 4.5 | 4.5 | 6 |
| Sulfur | 16.5 | 16.5 | 16.5 | 16.5 | 16.5 | 3 |
| Lithium Carbonate | 10.5 | 10.5 | 10.5 | 10.5 | 10.5 | 12 |
| Acronal TL 8821 (38% solid content) | 60 | — | — | — | — | — |

TABLE 3-continued

|  | Comparative Example 1 | Comparative Example 2 | Comparative Example 3 | Comparative Example 4 | Comparative Example 5 | Comparative Example 6 |
|---|---|---|---|---|---|---|
| Joncryl 77 (46% solid content) | — | 50 | — | — | — | — |
| NeoCryl A-1131 (40% solid content) | — | — | 65 | — | — | — |
| Joncryl 90 (44% solid content) | — | — | — | 59 | — | — |
| NeoRez R-986 (35% solid content) | — | — | — | — | 68.5 | — |
| Joncryl 678 (solid) | — | — | — | — | — | 24 |
| Water | 8.5 | 18.5 | 3.5 | 9.5 | — | — |
| Ammonia water | — | — | — | — | — | 55 |
| Total | 100 | 100 | 100 | 100 | 100 | 100 |
| Color changing composition (% by weight) | 31.5 | 31.5 | 31.5 | 31.5 | 31.5 | 21 |
| Solid content of aqueous resin composition (% by weight) | 22.8 | 23 | 26 | 25.96 | 24 | 24 |
| Total Solid content (% by weight) | 54.3 | 54.5 | 57.5 | 57.5 | 55.5 | 45 |
| Weight ratio of aqueous resin composition to color changing composition | 1:1.4 | 1:1.4 | 1:1.2 | 1:1.2 | 1:1.3 | 1:0.88 |

TABLE 4

|  | Example 1 | Example 2 |
|---|---|---|
| Bismuth Subsalicylate | 4.5 | 4.5 |
| Sulfur | 16.5 | 16.5 |
| Lithium Carbonate | 10.5 | 10.5 |
| NeoCryl A-1131 (40% solid content) | 60 | 50 |
| ACRONAL TL 8821 (38% solid content) | — | — |
| JONCRYL 77 (46% solid content) | — | 10 |
| Propylene glycol | 5 | 5 |
| Water | 3.5 | 3.5 |
| Total | 100 | 100 |
| Color changing composition (% by weight) | 31.5 | 31.5 |
| Solid content of aqueous resin composition (% by weight) | 24 | 24.6 |
| Total Solid content (% by weight) | 55.5 | 56.1 |
| Weight ratio of aqueous resin composition to color changing composition | 1:1.3 | 1:1.28 |

TABLE 5-1

|  | Comparative Example. 2 | Comparative Example. 4 | Comparative Example. 5 | Comparative Example. 7 | Comparative Example. 8 | Comparative Example. 9 | Comparative Example. 10 |
|---|---|---|---|---|---|---|---|
| Bismuth Subsalicylate | 4.5 | 4.5 | 4.5 | 4.5 | 4.5 | 4.5 | 4.5 |
| Sulfur | 16.5 | 16.5 | 16.5 | 16.5 | 16.5 | 16.5 | 16.5 |
| Lithium Carbonate | 10.5 | 10.5 | 10.5 | 10.5 | 10.5 | 10.5 | 7 |
| NeoCryl A-1131 (40% solid content) | — | — | — | — | — | 13 | — |
| JONCRYL 90 (44% solid content) | — | 59 | — | 54 | 54 | — | — |
| Joncryl HPE 2157 (48% solid content) | — | — | — | — | — | — | 49.5 |
| NeoRez R-986 (35% solid content) | — | — | 68.5 | — | — | — | — |

TABLE 5-1-continued

| | Comparative Example. 2 | Comparative Example. 4 | Comparative Example. 5 | Comparative Example. 7 | Comparative Example. 8 | Comparative Example. 9 | Comparative Example. 10 |
|---|---|---|---|---|---|---|---|
| JONCRYL 77 (46% solid content) | 50 | — | — | — | — | — | — |
| Propylene glycol | — | — | — | 5 | — | 2 | — |
| Ethylene glycol methyl ether | — | — | — | — | 5 | — | — |
| Propylene glycol butyl ether | — | — | — | — | — | — | 15 |
| Water | 18.5 | 9.5 | — | 9.5 | 9.5 | 53.5 | 7.5 |
| Total | 100 | 100 | 100 | 100 | 100 | 100 | 100 |
| Color changing composition (% by weight) | 31.5 | 31.5 | 31.5 | 31.5 | 31.5 | 31.5 | 28 |
| Solid content of aqueous resin composition (% by weight) | 23 | 25.96 | 24 | 23.76 | 23.76 | 5.2 | 23.76 |
| Total Solid content (% by weight) | 54.5 | 57.5 | 55.5 | 55.26 | 55.26 | 36.7 | 51.76 |
| Weight ratio of aqueous resin composition to color changing composition | 1:1.4 | 1:1.2 | 1:1.31 | 1:1.33 | 1:1.33 | 1:6 | 1:1.18 |

TABLE 5-2

| | Example 3 | Example 4 | Example 5 | Example 6 | Example 7 |
|---|---|---|---|---|---|
| Bismuth Subsalicylate | 5 | 4.5 | 4.5 | 4.5 | 4.5 |
| Sulfur | 5 | 16.5 | 16.5 | 16.5 | 16.5 |
| Lithium Carbonate | 10 | 10.5 | 10.5 | 9 | 7 |
| NeoCryl A-1131 (40% solid content) | 60 | — | — | — | — |
| Joncryl HPE 2157 (48% solid content) | — | 49.5 | 49.5 | 20.8 | 62.5 |
| NeoRez R-986 (35% solid content) | — | — | — | — | — |
| JONCRYL 77 (46% solid content) | — | — | — | — | — |
| Propylene glycol | 5 | — | — | 5 | — |
| Ethylene glycol methyl ether | — | — | 10 | — | 3.8 |
| Propylene glycol butyl ether | — | 1 | — | — | — |
| Water | 15 | 23.5 | 14.5 | 44.2 | 5.7 |
| Total | 100 | 100 | 100 | 100 | 100 |
| Color changing composition (% by weight) | 20 | 31.5 | 31.5 | 30 | 28 |
| Solid content of aqueous resin composition (% by weight) | 24 | 23.76 | 23.76 | 10 | 30 |
| Total Solid content (% by weight) | 44 | 55.26 | 55.26 | 40 | 58 |
| Weight ratio of aqueous resin composition to color changing composition | 1:0.83 | 1:1.33 | 1:1.33 | 1:3 | 1:1.05 |

Test for Autoclave Indicating Effect of Chemical Indicating Composition

The autoclave indicating effect of chemical indicating compositions in Comparative Example 1-10 and Example 1-7 were tested according to the procedure of "test for autoclave indicating effect of chemical indicating composition" described above, all the autoclave indicating effects of chemical indicating compositions, which were provided in Comparative Example 1-9 and Example 1-7, met the requirement of ISO 11140-1; In the chemical indicating composition provided in Comparative Example 10, the weight percent of the film-forming agent was higher than 10%, therefore, the chemical indicating composition was not stable enough, accordingly, the autoclave indicating effect did not meet the requirement of ISO 11140-1.

Immediate Adhesion Test for Chemical Indicating Composition

Following the procedure described above for "Immediate adhesion test", the adhesion of chemical indicating compositions, which were provided in Comparative Example 3, 4, 6 and Example 1-7 were tested, and the test results were shown in Table 6.

Comparative Examples 3 and 4, in which chemical indicating composition only comprised first aqueous resin composition, had adhesion scores lower than 4, for both the paper substrate and the polyester substrate.

Examples 1, 3, 4, 5, 6 and 7, in which chemical indicating composition comprised first aqueous resin composition and film-forming agent, had adhesion scores of 4 or more, for both the paper substrate and the polyester substrate.

Examples 2, in which chemical indicating composition comprised first aqueous resin composition, second aqueous resin composition and film-forming agent, had adhesion scores of 4 or more, for both the paper substrate and the polyester substrate.

Comparative Example 6, in which the molecular weight of aqueous resin composition in the chemical indicating composition is lower than 20,000, had adhesion scores lower than 4, for both the paper substrate and the polyester substrate.

TABLE 6

|  | First aqueous resin composition | Second aqueous resin composition or film-forming agent | Adhesion between chemical indicating composition and paper substrate | Adhesion between chemical indicating composition and polyester substrate |
|---|---|---|---|---|
| Comparative Example 3 | NeoCryl A-1131 | — | 3.5 | 3.5 |
| Comparative Example 4 | JONCRYL 90 | — | 3.5 | 3 |
| Comparative Example 6 | JONCRYL 678 | — | 2 | 3.5 |
| Example 1 | NeoCryl A-1131 | Propylene glycol | 4 | 5 |
| Example 2 | NeoCryl A-1131 | JONCRYL 77 and propylene glycol | 5 | 5 |
| Example 3 | NeoCryl A-1131 | propylene glycol | 4.5 | 5 |
| Example 4 | Joncryl HPE 2157 | Propylene glycol butyl ether | 4 | 5 |
| Example 5 | Joncryl HPE 2157 | Propylene glycol | 4 | 5 |
| Example 6 | Joncryl HPE 2157 | Propylene glycol | 4 | 4.5 |
| Example 7 | Joncryl HPE 2157 | Ethylene glycol methyl ether | 4 | 5 |

Note:
JONCRYL 678 in Comparative Example 6 is not an aqueous resin composition in form of polymer emulsion or polymer dispersion, but a water-soluble resin solid.

Test for Transfer of Chemical Indicating Composition to Adhesive

Following the procedure described for "Blocking test for transfer of the chemical indicating composition from the surface of the autoclave process tape to its adhesive" above, the transfer of chemical indicating compositions, which were provided in Comparative Examples 9 and Examples 1-7, were tested, and the results were shown in Table 7 below.

As seen from the tested results shown in Table 7, the weight ratio between the solid content of aqueous resin composition and color changing composition is an important factor influencing the transfer of chemical indicating composition to adhesive. When the ratio is lower than 1:3, the transfer ratio of chemical indicating composition to adhesive is high, not meeting the requirement. And when the ratio is higher than 1:3, the transfer ratio of chemical indicating composition to adhesive is low, meeting the requirement.

In Examples 1-7, the weight ratio between the solid content of aqueous resin composition and color changing composition in the chemical indicating composition is higher than 1:3, and the scores in test for transfer were 4 or more, indicating that the transfer ratio of chemical indicating composition to adhesive is low, meeting the requirement.

In Comparative Examples 9, the weight ratio between the solid content of aqueous resin composition and color changing composition in the chemical indicating composition is lower than 1:3, and the score in test for transfer was lower than 4, indicating that the transfer ratio of chemical indicating composition to adhesive is high, not meeting the requirement.

TABLE 7

|  | First aqueous resin composition | Second aqueous resin composition or film-forming agent | Weight ratio between solid content of aqueous resin composition and color changing composition | Transfer of chemical indicating composition to adhesive |
|---|---|---|---|---|
| Comparative Examples 9 | NeoCryl A-1131 | Propylene glycol | 1:6 | 1 |
| Example 1 | NeoCryl A-1131 | Propylene glycol | 1:1.3 | 4.5 |
| Example 2 | NeoCryl A-1131 | JONCRYL 77 and propylene glycol | 1:1.28 | 4.5 |
| Example 3 | NeoCryl A-1131 | Propylene glycol | 1:0.83 | 4.5 |
| Example 4 | Joncryl HPE 2157 | Propylene glycol butyl ether | 1:1.33 | 4 |

TABLE 7-continued

| | First aqueous resin composition | Second aqueous resin composition or film-forming agent | Weight ratio between solid content of aqueous resin composition and color changing composition | Transfer of chemical indicating composition to adhesive |
|---|---|---|---|---|
| Example 5 | Joncryl HPE 2157 | Propylene glycol | 1:1.33 | 4 |
| Example 6 | Joncryl HPE 2157 | Propylene glycol | 1:3 | 4 |
| Example 7 | Joncryl HPE 2157 | Ethylene glycol methyl ether | 1:1.05 | 4.5 |

Water Resistance Test of Chemical Indicating Composition

Following the procedure described for "water resistance test of chemical indicating composition" above, the water resistance of the chemical indicating compositions, which were provided in Comparative Examples 7-8 and Examples 1-7, were tested and the results were shown in Table 8 below.

As seen from the results shown in Table 8, the acid value of aqueous resin composition was an important factor affecting the water resistance of chemical indicating composition. The higher acid value the aqueous resin composition had, the poorer water resistance of chemical indicating composition was. The lower acid value the aqueous resin composition had, the better water resistance of chemical indicating composition was.

In Examples 1-7, the acid values of aqueous resin compositions in chemical indicating compositions were all lower than 60, their scores in wet scuff resistance test were higher than 4, and scores in boiling resistance test were higher than 3, indicating that these chemical indicating compositions had good water resistance.

In Comparative Examples 7-8, the acid values of aqueous resin compositions in chemical indicating compositions were all higher than 60, and their scores in wet scuff resistance test were passable, but scores in boiling resistance test were lower than 3, indicating inferior water resistance of the chemical indicating compositions.

TABLE 8

| | First aqueous resin composition | Second aqueous resin composition or film-forming agent | Indicating tag | | Indicating tape | |
|---|---|---|---|---|---|---|
| | | | wet scuff resistance test | boiling resistance test | wet scuff resistance test | boiling resistance test |
| Comparative Example 7 | JONCRYL 90 | Propylene glycol | 4 | 1 | 4.5 | 2.5 |
| Comparative Example 8 | JONCRYL 90 | Ethylene glycol methyl ether | 3.5 | 1 | 4.5 | 2.5 |
| Example 1 | NeoCryl A-1131 | Propylene glycol | 5 | 5 | 5 | 4.5 |
| Example 2 | NeoCryl A-1131 | JONCRYL 77 and propylene glycol | 5 | 5 | 5 | 3 |
| Example 3 | NeoCryl A-1131 | Propylene glycol | 5 | 5 | 5 | 4.5 |
| Example 4 | Joncryl HPE 2157 | Propylene glycolbutyl ether | 3.5 | 1.5 | 4.5 | 3 |
| Example 5 | Joncryl HPE 2157 | Ethylene glycol methyl ether | 3.5 | 2 | 4.5 | 3 |
| Example 6 | Joncryl HPE 2157 | Propylene glycol | 3.5 | 1 | 4 | 2.5 |
| Example 7 | Joncryl HPE 2157 | Ethylene glycol methyl ether | 3.5 | 3 | 5 | 3.5 |

Transfer Test of Chemical Indicating Composition to Wrap

Following the procedure described for "transfer test of chemical indicating composition to wrap" above, transfer of chemical indicating compositions, which were provided in Comparative Examples 1, 2, 5, 7, 8, and Examples 1-7, to wrap were tested, and the results were shown in table 9 below.

As seen from the results shown in Table 9, the acid value of aqueous resin composition was an important factor influencing the transfer of chemical indicating composition to wrap. The higher acid value the aqueous resin composition had, the severer transfer of chemical indicating composition was, thereby not meeting requirement. The lower acid value the aqueous resin composition had, the lower water transfer of chemical indicating composition was, thereby meeting requirement.

In Comparative Examples 7 and 8, the acid values of aqueous resin compositions in chemical indicating compositions were all higher than 60, and the scores in transfer test of chemical indicating composition to wrap (indicating tape) were all lower than 4, indicating a higher transfer ratio of the chemical indicating composition to wrap (indicating tape), not meeting requirement.

In Examples 1-7, the acid values of aqueous resin compositions in chemical indicating compositions were all lower than 60, and the scores in transfer test of chemical indicating composition to wrap (indicating tape) were all higher than 4, indicating a lower transfer ratio of the chemical indicating composition to wrap (indicating tape), meeting requirement.

In Comparative Examples 1, 2 and 5, the chemical indicating compositions did not comprise first aqueous resin composition, and therefore the scores in transfer test of chemical indicating composition to wrap (indicating tape) were all lower than 4, indicating a higher transfer ratio of the chemical indicating composition to wrap (indicating tape), not meeting requirement.

TABLE 9

| | First aqueous resin composition | Second aqueous resin composition or film-forming agent | transfer of chemical indicating composition to indicating tape |
|---|---|---|---|
| Comparative Example 1 | — | ACRONAL TL 8821 | 3 |
| Comparative Example 2 | — | JONCRYL 77 | 2 |
| Comparative Example 5 | — | NeoRez R-986 | 1 |
| Comparative Example 7 | JONCRYL 90 | Propylene glycol | 3-3.5 |
| Comparative Example 8 | JONCRYL 90 | Ethylene glycol methyl ether | 3-3.5 |
| Example 1 | NeoCryl A-1131 | Propylene glycol | 4-4.5 |
| Example 2 | NeoCryl A-1131 | JONCRYL 77 and propylene glycol | 4-4.5 |
| Example 3 | JONCRYL 90 | Propylene glycol | 4-4.5 |
| Example 4 | Joncryl HPE 2157 | Propylene glycol butyl ether | 4 |
| Example 5 | Joncryl HPE 2157 | Ethylene glycol methyl ether | 4 |
| Example 6 | Joncryl HPE 2157 | Propylene glycol | 4 |
| Example 7 | Joncryl HPE 2157 | Ethylene glycol methyl ether | 4-4.5 |

To sum up, the chemical indicating composition of the present disclosure has good adhesion to substrate, such that the chemical indicating composition can be coated on the substrate to prepare an autoclave process indicator. The chemical indicating composition also has good water resistance. Additionally, the chemical indicating composition has less contamination to the adhesive in the autoclave process indicator, due to the low transfer of the chemical indicating composition to the adhesive. And the transfer of the chemical indicating composition to sterilization wrap is also low, and thus less contamination is caused to the wrap. Furthermore, chemical indicating composition of the present disclosure is an aqueous system with low viscosity and high solid content, and consequently is environmental friendly and safe to handle.

Although the above embodiments contain many specific details for the purpose of illustration, a person skilled in the art would appreciate that the various alterations, modifications, substitutions and changes of these details are all within the scope claimed by the present disclosure. Therefore, the disclosures described in the specific embodiments have no limitations on the scope claimed by the present disclosure. The proper scope of the present disclosure is defined by the claims and equivalent thereof set forth as follows. All references cited are incorporated herein by reference in their entirety.

The invention claimed is:

1. A chemical indicating composition, comprising:
   an aqueous resin in a form of a polymer emulsion or a polymer dispersion, having a molecular weight of 20,000 or more, an acid value of 60 or less and a boil resistance of 3 or more, the aqueous resin comprising a first aqueous resin composition having a minimum film-forming temperature of 30° C. or more and a second aqueous resin composition having a minimum film-forming temperature lower than 30° C.;
   a film-forming agent;
   a color changing composition; and
   water as a solvent,
   wherein, based on total weight of the chemical indicating composition,
   the solid weight percentage of the first aqueous resin composition is 10-30%,
   the solid weight percentage of the second aqueous resin composition is 0-35%,
   the weight percentage of the film-forming agent is 1-10%,
   the weight percentage of the color changing composition is 15-40%,
   the total weight percentage of the water contained in the aqueous resin and the water as a solvent is 20-70%, and
   the solid content of the aqueous resin and the color changing composition are in a weight ratio of 1:3 or greater.

2. The chemical indicating composition according to claim 1, wherein at least one of the first aqueous resin composition and the second aqueous resin composition comprises at least one of an anionic acrylic polymer emulsion, a styrene acrylic polymer emulsion or polymer dispersion, a silicone modified acrylic polymer emulsion, an acrylic modified polyurethane polymer emulsion, a silicone modified polyurethane polymer emulsion, and a polycarbonate modified polyurethane polymer emulsion.

3. The chemical indicating composition according to claim 1, wherein the first aqueous resin composition has a minimum film-forming temperature of 60° C. or more.

4. The chemical indicating composition according to claim 1, wherein the film-forming agent comprises at least one of a C6-12 organic hydrocarbon compound, a C3-16 organic compound which contains an alcohol functional group, a C3-16 organic compound which contains an ether functional group, a C3-16 organic compound which contains an ester functional group, and a C3-16 organic compound which contains a keto functional group.

5. The chemical indicating composition according to claim 1, wherein the color changing composition comprises a polyvalent metal compound, a sulfur source, and a compound capable of generating alkaline conditions when exposed to steam at a high temperature.

6. The chemical indicating composition according to claim 1, wherein the weight percentage of the film-forming agent is 2-5%.

7. The chemical indicating composition according to claim 1, wherein the weight percentage of the color changing composition is 20-35%.

8. An autoclave process indicator, comprising a substrate and the chemical indicating composition according to claim 1 coated on the substrate.

9. The autoclave process indicator according to claim 8, wherein the substrate comprises at least one of a tape, a plastic film, a paper, and a nonwoven fabric.

10. The autoclave process indicator according to claim 8, wherein the substrate comprises an adhesive tape comprising an adhesive surface and a non-adhesive surface, and wherein the chemical indicating composition is coated on the non-adhesive surface of the tape.

11. A method for preparing an autoclave process indicator, the method comprising:
coating the chemical indicating composition according to claim 1 onto a surface of a substrate to form an autoclave process indicator.

12. The method according to claim 11, wherein the substrate comprises an adhesive tape comprising an adhesive surface and a non-adhesive surface, and wherein the chemical indicating composition is coated on the non-adhesive surface of the tape.

13. The method according to claim 11, further comprising: heating the autoclave process indicator.

14. An autoclave process indicator, comprising a substrate and the chemical indicating composition according to claim 2 coated on the substrate.

15. An autoclave process indicator, comprising a substrate and the chemical indicating composition according to claim 3 coated on the substrate.

16. An autoclave process indicator, comprising a substrate and the chemical indicating composition according to claim 4 coated on the substrate.

17. An autoclave process indicator, comprising a substrate and the chemical indicating composition according to claim 5 coated on the substrate.

18. An autoclave process indicator, comprising a substrate and the chemical indicating composition according to claim 6 coated on the substrate.

19. An autoclave process indicator, comprising a substrate and the chemical indicating composition according to claim 7 coated on the substrate.

20. A method for preparing an autoclave process indicator, the method comprising:
coating the chemical indicating composition according to claim 2 onto a surface of a substrate to form an autoclave process indicator.

* * * * *